United States Patent
Suzuki

(10) Patent No.: US 12,066,418 B2
(45) Date of Patent: Aug. 20, 2024

(54) METHOD FOR MEASURING CONCENTRATION OF FLUORINE GAS CONTAINED IN HALOGEN FLUORIDE-CONTAINING GAS BY ULTRA VIOLET SPECTROSCOPY

(71) Applicant: SHOWA DENKO K.K., Tokyo (JP)

(72) Inventor: Atsushi Suzuki, Tokyo (JP)

(73) Assignee: Resonac Corporation, Tokyo (JP)

( * ) Notice: Subject to any disclaimer, the term of this patent is extended or adjusted under 35 U.S.C. 154(b) by 475 days.

(21) Appl. No.: 17/609,211

(22) PCT Filed: Nov. 12, 2020

(86) PCT No.: PCT/JP2020/042275
§ 371 (c)(1),
(2) Date: Nov. 5, 2021

(87) PCT Pub. No.: WO2021/106602
PCT Pub. Date: Jun. 3, 2021

(65) Prior Publication Data
US 2022/0214323 A1    Jul. 7, 2022

(30) Foreign Application Priority Data

Nov. 27, 2019   (JP) .................................. 2019-214261

(51) Int. Cl.
*G01N 33/00*     (2006.01)
*G01N 21/01*     (2006.01)
(Continued)

(52) U.S. Cl.
CPC ......... *G01N 33/0052* (2013.01); *G01N 21/01* (2013.01); *G01N 21/255* (2013.01);
(Continued)

(58) Field of Classification Search
CPC .... G01N 21/01; G01N 21/255; G01N 21/314; G01N 21/33; G01N 33/0052; G01N 2021/0112
See application file for complete search history.

(56) References Cited

U.S. PATENT DOCUMENTS

| 5,534,107 A | 7/1996 | Gray et al. |
| 6,686,594 B2 | 2/2004 | Ji et al. |
| (Continued) | | |

FOREIGN PATENT DOCUMENTS

| CN | 103575685 A | 2/2014 |
| EP | 0 697 715 A1 | 2/1996 |
| (Continued) | | |

OTHER PUBLICATIONS

International Search Report dated Jan. 12, 2021 in Application No. PCT/JP2020/042275.

(Continued)

*Primary Examiner* — Mark R Gaworecki
(74) *Attorney, Agent, or Firm* — Sughrue Mion, PLLC

(57) ABSTRACT

A method for measuring the concentration of fluorine gas, which includes irradiating a halogen fluoride-containing gas with ultraviolet light in which the ratio ($W_X/W_F$) of the maximum value ($W_X$) of ultraviolet light intensity in the wavelength region of less than 250 nm with respect to the ultraviolet light intensity ($W_F$) at a wavelength of 285 nm is 1/10 or less, and measuring the absorbance at a wavelength of 285 nm to obtain the concentration of fluorine gas contained in the halogen fluoride-containing gas.

8 Claims, 1 Drawing Sheet

(51) Int. Cl.
  *G01N 21/25*  (2006.01)
  *G01N 21/31*  (2006.01)
  *G01N 21/33*  (2006.01)

(52) U.S. Cl.
  CPC .......... *G01N 21/314* (2013.01); *G01N 21/33* (2013.01); *G01N 2021/0112* (2013.01)

(56) References Cited

U.S. PATENT DOCUMENTS

| 7,192,875 | B1 | 3/2007 | Cook |
| 10,287,499 | B2 | 5/2019 | Takahashi et al. |
| 2003/0098419 | A1 | 5/2003 | Ji et al. |
| 2005/0115674 | A1 | 6/2005 | Taguchi et al. |
| 2012/0228144 | A1 | 9/2012 | Pernice et al. |
| 2018/0251679 | A1 | 9/2018 | Takahashi et al. |

FOREIGN PATENT DOCUMENTS

| JP | 5-275399 | A | 10/1993 |
| JP | 8-107090 | A | 4/1996 |
| JP | 2003-236337 | A | 8/2003 |
| JP | 2008-196882 | A | 8/2008 |
| JP | 2010-203855 | A | 9/2010 |
| JP | 2013-507629 | A | 3/2013 |
| JP | 5221881 | B2 | 6/2013 |
| WO | 2016/056300 | A1 | 4/2016 |

OTHER PUBLICATIONS

Written Opinion of the International Searching Authority Jan. 12, 2021 in Application No. PCT/JP2020/042275.

Shao, et al., "Experimental Study of the Influence of Temperatures on $NO_2$ Differential Absorption Spectrum Characteristics", Journal of Engineering for Thermal Energy and Power, Jul. 2008, vol. 23, No. 4, pp. 404-407, 444 (5 pages total).

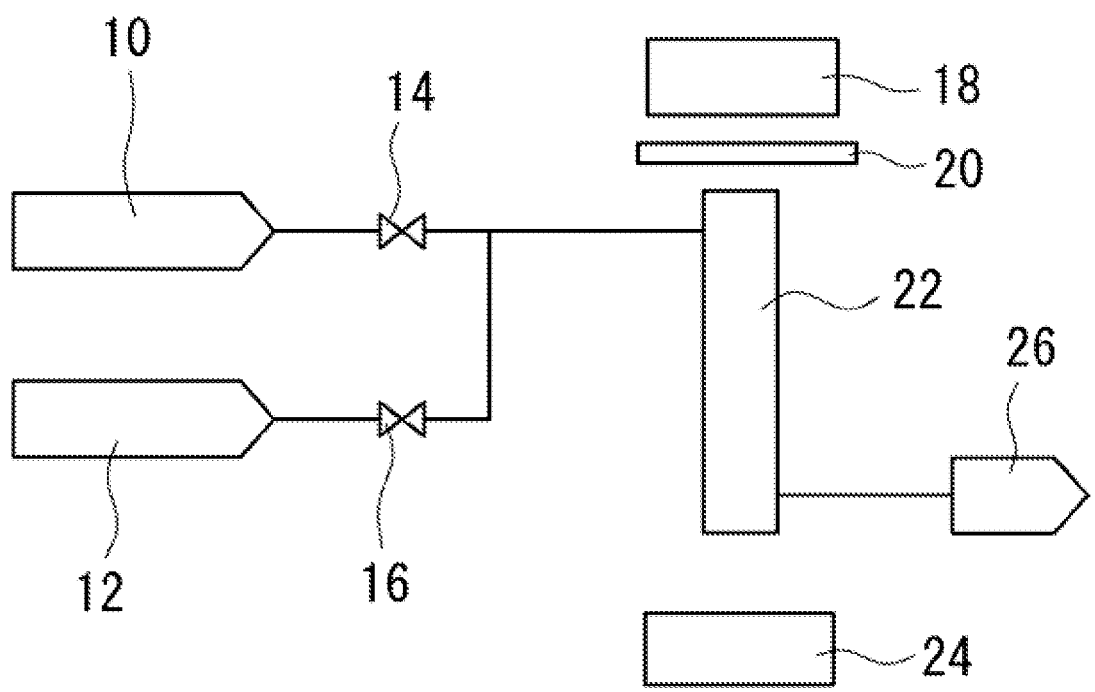

METHOD FOR MEASURING CONCENTRATION OF FLUORINE GAS CONTAINED IN HALOGEN FLUORIDE-CONTAINING GAS BY ULTRA VIOLET SPECTROSCOPY

CROSS REFERENCE TO RELATED APPLICATIONS

This application is a National Stage of International Application No. PCT/JP2020/042275 filed Nov. 12, 2020, claiming priority based on Japanese Patent Application No. 2019-214261 filed Nov. 27, 2019.

TECHNICAL FIELD

The present invention relates to a method for measuring the concentration of fluorine gas contained in a halogen fluoride-containing gas.

BACKGROUND ART

Halogen fluorides are used in for example etching gas and cleaning gas in semiconductor manufacturing processes. In recent years, the miniaturization of semiconductors is in progress, and it is required that etching gas and cleaning gas for example used in semiconductor manufacturing processes be high-purity gas. To prepare high-purity gas, a method for measuring the concentration of fluorine gas, which is an impurity, contained in etching gas and cleaning gas for example with good accuracy is needed.

As a method for measuring the concentration of fluorine gas, for example, Patent Literature 1 discloses a method in which the concentration of fluorine gas contained in a gas such as exhaust gas released from an electronic device manufacturing apparatus such as a semiconductor manufacturing apparatus is measured by using an ultraviolet spectrophotometer and a Fourier transform infrared spectrophotometer. Patent Literature 2 discloses a method in which the concentration of fluorine in exhaust gas released from a semiconductor process apparatus that uses sulfur hexafluoride is measured by using an ultraviolet spectrophotometer and a Fourier transform infrared spectrophotometer. Patent Literature 3 discloses a method in which halogen gas generated from a semiconductor manufacturing process is analyzed by ultraviolet-visible absorption spectroscopy.

CITATION LIST

Patent Literature

Patent Literature 1: JP 5221881 B2
Patent Literature 2: JP 2010-203855 A
Patent Literature 3: U.S. Pat. No. 6,686,594 B2

SUMMARY OF INVENTION

Technical Problem

In the case where the concentration of fluorine gas contained in a halogen fluoride-containing gas is measured by ultraviolet spectroscopy, since the halogen fluoride absorbs mainly light of wavelengths of less than 250 nm, part of the halogen fluoride is photolyzed, and fluorine molecules or fluorine radicals are generated. Hence, there has been a problem that, when measuring the concentration of fluorine gas in a halogen fluoride, measurement errors occur because of fluorine or fluorine radicals generated by photolysis.

Thus, an object of the present invention is to provide a high-accuracy measurement method that, in the measurement of the concentration of fluorine gas contained in a halogen fluoride-containing gas using an ultraviolet spectrophotometer, reduces the amount of measurement errors caused by for example fluorine gas generated by photolysis of the halogen fluoride.

Solution to Problem

The present inventor and others conducted extensive studies in order to solve the issue mentioned above, and have found out that, when measuring the concentration of fluorine gas contained in a halogen fluoride-containing gas by irradiating ultraviolet light, high-accuracy measurement can be made by suppressing irradiation with ultraviolet light of wavelengths of less than 250 nm and thus have completed the present invention. That is, the present invention includes [1] to [8] shown below.

[1] A method for measuring a concentration of fluorine gas, the method comprising irradiating a halogen fluoride-containing gas with ultraviolet light in which a ratio ($W_X/W_F$) of a maximum value ($W_X$) of ultraviolet light intensity in a wavelength region of less than 250 nm with respect to an ultraviolet light intensity ($W_F$) at a wavelength of 285 nm is 1/10 or less, and measuring an absorbance at a wavelength of 285 nm to obtain a concentration of fluorine gas contained in the halogen fluoride-containing gas.

[2] The method for measuring a concentration of fluorine gas according to [1], in which, using a means for suppressing irradiation with ultraviolet light of wavelengths of less than 250 nm, the halogen fluoride-containing gas is irradiated with ultraviolet light of wavelengths of not less than 250 nm from a light source.

[3] The method for measuring a concentration of fluorine gas according to claim 1 or 2, wherein the means is to irradiate the ultraviolet light irradiated from the light source to the halogen fluoride-containing gas via a filter that blocks at least 50% of the ultraviolet light with a wavelength of less than 250 nm and transmits at least 90% of the ultraviolet light with a wavelength of 280-290 nm.

[4] The method for measuring a concentration of fluorine gas according to any one of [1] to [3], in which the halogen fluoride is one kind of gas selected from the group consisting of chlorine trifluoride, bromine pentafluoride, iodine heptafluoride, bromine trifluoride, and iodine pentafluoride.

[5] The method for measuring a concentration of fluorine gas according to any one of [1] to [4], in which the halogen fluoride is iodine heptafluoride.

[6] The method for measuring a concentration of fluorine gas according to any one of [1] to [4], in which the halogen fluoride is bromine pentafluoride, and the maximum value ($W_X$) of ultraviolet light intensity in the wavelength region of less than 250 nm is a maximum value of ultraviolet light intensity in a wavelength region of less than 225 nm.

[7] The method for measuring a concentration of fluorine gas according to any one of [1] to [4], in which the halogen fluoride is chlorine trifluoride, and the maximum value ($W_X$) of ultraviolet light intensity in the wavelength region of less than 250 nm is a maximum value of ultraviolet light intensity in a wavelength region of less than 215 nm.

[8] The method for measuring a concentration of fluorine gas according to any one of [1] to [7], in which an absorption spectrum measured by irradiating a reference gas with the ultraviolet light is subtracted from an absorption spectrum measured by irradiating the halogen fluoride-containing gas with the ultraviolet light, and the concentration of fluorine gas is obtained from an absorbance at a wavelength of 285 nm of an obtained absorption spectrum.

Advantageous Effects of Invention

According to the present invention, high-accuracy measurement can be made for the concentration of fluorine gas contained in a halogen fluoride-containing gas.

BRIEF DESCRIPTION OF DRAWINGS

The FIGURE is a schematic diagram of an example of an analysis apparatus used for measurement of the concentration of fluorine gas of the present invention.

DESCRIPTION OF EMBODIMENTS

Hereinbelow, the present invention is described in detail, with reference to the FIGURE as necessary. The analysis apparatus used in the present invention is not limited to the analysis apparatus shown in the FIGURE.

The present invention relates to a method for measuring the concentration of fluorine gas, the method comprising irradiating a halogen fluoride-containing gas with ultraviolet light in which the ratio (WX/WF) of the maximum value (WX) of ultraviolet light intensity in the wavelength region of less than 250 nm with respect to the ultraviolet light intensity (WF) at a wavelength of 285 nm is 1/10 or less, and measuring the absorbance at a wavelength of 285 nm to obtain the concentration of fluorine gas contained in the halogen fluoride-containing gas.

<Gas to be Measured, Equipment and Others Used for Measurement of the Concentration of Fluorine Gas>
(Halogen Fluoride-Containing Gas)

The halogen fluoride contained in the halogen fluoride-containing gas used in an embodiment of the present invention is a fluorine compound containing a halogen such as chlorine, bromine, or iodine as a constituent element. Examples of the halogen fluoride include chlorine fluoride, chlorine trifluoride, bromine fluoride, bromine trifluoride, bromine pentafluoride, iodine fluoride, iodine trifluoride, iodine pentafluoride, and iodine heptafluoride. Among these, in terms of etching properties and cleaning properties, chlorine trifluoride, bromine trifluoride, bromine pentafluoride, iodine pentafluoride, and iodine heptafluoride are preferable, and chlorine trifluoride, iodine heptafluoride, and bromine pentafluoride can be used for the present invention more favorably. In the halogen fluoride-containing gas, one kind of halogen fluoride may be contained singly, or a plurality of kinds may be contained.

Fluorine gas, which is to be measured, and impurity gases other than fluorine gas may be contained in the halogen fluoride-containing gas. Examples of impurity gases include helium, argon, oxygen gas ($O_2$), nitrogen gas ($N_2$), carbon dioxide, and carbon tetrafluoride. One single kind or a plurality of kinds of impurity gas may be contained in the halogen fluoride-containing gas, and the amount of impurity gas contained is not particularly limited.

Further, a diluent gas may be contained in the halogen fluoride-containing gas. The diluent gas is a gas inert to the halogen fluoride, the fluorine-containing gas, and the impurity gas mentioned above. Examples of the diluent gas include helium, argon, nitrogen gas ($N_2$), carbon dioxide, and carbon tetrafluoride. One single kind or a plurality of kinds of diluent gas may be contained in the halogen fluoride-containing gas, and the amount of diluent gas contained is not particularly limited.

The halogen fluoride-containing gas is introduced into a gas cell 22 described later from a halogen fluoride-containing gas supply source 10 via a valve 14. The supply method, form, size, for example, of the halogen fluoride-containing gas supply source 10 are not particularly limited as long as the halogen fluoride-containing gas supply source 10 can supply a halogen fluoride-containing gas to the gas cell 22. For example, a halogen fluoride-containing gas may be supplied to the gas cell 22 from a branch pipe branched from a halogen fluoride-containing gas supply pipe connected to an etching apparatus used in a semiconductor manufacturing process via the valve 14, or may be supplied to the gas cell 22 from a container such as a gas cylinder in which the same halogen fluoride-containing gas as the gas supplied to an etching apparatus is retained.

(Reference Gas)

When irradiating the halogen fluoride-containing gas mentioned above with ultraviolet light by a method described later and measuring the absorption spectrum, it is preferable to use a reference gas as a blank and measure the absorption spectrum of the reference gas in the gas cell 22 described later. The reference gas is not particularly limited as long as the reference gas does not contain a component that absorbs wavelengths around 285 nm. Examples of the reference gas include nitrogen gas ($N_2$) and helium gas.

The reference gas is introduced into the gas cell 22 from a reference gas supply source 12 via a valve 16. The supply method, form, size, for example, of the reference gas supply source 12 are not particularly limited as long as a reference gas can be supplied to the gas cell 22. For example, a reference gas may be supplied to the gas cell 22 from a container such as a gas cylinder in which the reference gas is retained.

(Light Source 18)

A light source 18 used in an embodiment of the present invention is used to irradiate ultraviolet light onto the halogen fluoride-containing gas and the reference gas mentioned above. The light source 18 is not particularly limited as long as the light source 18 is one that emits ultraviolet light including a wavelength of 285 nm; for example, the light source such as a deuterium lamp, a xenon lamp, a mercury lamp (low pressure or high pressure), a metal halide lamp, a fluorescent lamp, a black light (a blue lamp) may be used, and also a light beam with few light components of wavelengths of less than 250 nm may be used.

(Filter 20)

In an embodiment of the present invention, when using a means for suppressing irradiation with ultraviolet light of wavelengths of less than 250 nm, it is preferable that the ultraviolet light irradiated from the light source 18 mentioned above be irradiated onto the halogen fluoride via a filter 20, in terms of being able to suppress the photolysis of the halogen fluoride with good efficiency. The filter 20 is not particularly limited as long as the filter 20 can block ultraviolet light of wavelengths of less than 250 nm sufficiently; the filter 20 is preferably one that can block 50% or more of ultraviolet light of wavelengths of less than 250 nm, more preferably one that can block 60% or more, and still more preferably one that can block 70% or more are used. By irradiating ultraviolet light via the filter 20, a reduction in measurement accuracy due to for example fluorine gas generated by photolysis of a halogen fluoride that has the maximum absorption wavelength in the wavelength region of less than 250 nm can be suppressed.

As the filter 20, a filter that sufficiently transmits ultraviolet light including a wavelength of 285 nm, which is the wavelength of the maximum absorption of fluorine, is preferably used in terms of being able to make high-accuracy measurement; it is desirable for the filter 20 to transmit preferably 90% or more of ultraviolet light of wavelengths of 280 to 290 nm, and more preferably 95% or more. The filter 20 is not particularly limited as long as the filter 20 has the properties mentioned above; for example, a commercially available product such as a short wavelength cut filter manufactured by Asahi Spectra Co., Ltd. may be used.

(Gas Cell 22)

The gas cell 22 is used to allow the halogen fluoride-containing gas and the reference gas mentioned above to be irradiated with ultraviolet light while being enclosed or distributed. In the gas cell 22, the main body of the gas cell is provided with a gas inlet, a gas exhaust port connected to an outlet 26, an entrance window, an exit window, for example. The material of the main body of the gas cell 22 other than the entrance window or the exit window is not particularly limited as long as it is a material that exhibits corrosion resistance to the components contained in the halogen fluoride-containing gas and fluorine gas; for example, stainless steel, nickel, Inconel, or Monel may be used.

The material of the entrance window and the exit window is not particularly limited as long as it is a material that does not absorb light of wavelengths around 285 nm and that exhibits corrosion resistance to the halogen fluoride-containing gas and the fluorine-containing gas; for example, calcium fluoride or barium fluoride may be used.

(Spectroscope 24)

A spectroscope 24 measures the absorption spectrum of the wavelengths of ultraviolet light emitted from the exit window of the gas cell 22 mentioned above. The spectroscope 24 is not particularly limited as long as the spectroscope 24 can measure the absorption spectrum of ultraviolet light; for example, an ultraviolet spectrophotometer commonly used in the field of the present invention may be used.

(Others)

In order to take light sent from the light source 18 into the gas cell 22 with good efficiency, a lens for example may be provided between the emission end of the light source 18 and the entrance window of the gas cell 22.

<Method for Measuring the Concentration of Fluorine Gas>

Hereinbelow, a method for measuring the concentration of fluorine gas of the present invention using the gas to be measured, the equipment and others described above is described.

(1) Measurement of the Reference Gas

The absorption spectrum of the reference gas is preferably measured in advance in order to measure the concentration of fluorine gas contained in the halogen fluoride-containing gas of the present invention. To measure the absorption spectrum of the reference gas, the valve 14 is closed to prevent halogen fluoride-containing gas from being supplied from the halogen fluoride-containing gas supply source 10, and the valve 16 is opened to introduce the reference gas into the gas cell 22 from the reference gas supply source 12. The introduction of the reference gas may be performed such that the reference gas is distributed through the gas cell 22 while the outlet 26 is kept open, or may be performed such that the outlet 26 is closed and the reference gas is enclosed in the gas cell 22.

Ultraviolet light emitted from the light source 18 is irradiated onto the reference gas in the gas cell 22 from the entrance window of the gas cell 22, preferably via the filter 20. At this time, the ultraviolet light of the light source 18 may be irradiated onto the entrance window of the gas cell 22 via an optical fiber. Ozone may be generated from oxygen in the air because of ultraviolet light of short wavelengths, and may affect the measurement; thus, it is preferable that a purge gas such as nitrogen be supplied to and around the entrance window or that an airtight structure be employed so that oxygen and air for example do not get in from the entrance window or the exit window.

Moreover, it is necessary that the ratio ($W_X/W_F$) (hereinafter, also referred to as "the ultraviolet light intensity ratio") of the maximum value ($W_X$) of ultraviolet light intensity in the wavelength region of less than 250 nm with respect to the ultraviolet light intensity ($W_F$) at a wavelength of 285 nm of ultraviolet light irradiated from the light source 18 onto the reference gas and the halogen fluoride-containing gas be 1/10 or less. Thereby, a situation where the halogen fluoride is photolyzed by irradiation with ultraviolet light of wavelengths of less than 250 nm and the resulting fluorine gas reduces measurement accuracy can be suppressed. The ultraviolet light intensity ratio ($W_X/W_F$) mentioned above is more preferably 1/15 or less. The maximum value of ultraviolet light intensity in the wavelength region of less than 250 nm is, in other words, the intensity of ultraviolet light at a wavelength of the highest intensity out of ultraviolet light of wavelengths of less than 250 nm. The $W_F$ and $W_X$ mentioned above can be measured by the spectroscope 24 mentioned above. The ultraviolet light intensity ratio mentioned above can be adjusted with the light source 18 and the filter 20.

Within the range mentioned above, the ultraviolet light intensity ratio mentioned above may be set in accordance with the wavelength of absorption of the halogen fluoride, as appropriate. For example, the wavelength of the maximum absorption of bromine pentafluoride is 217 nm; the maximum value of ultraviolet light intensity of the wavelength region shorter than a wavelength of the maximum absorption wavelength mentioned above plus 7 to 9 nm, for example the maximum value of ultraviolet light intensity of the wavelength region of less than 225 nm, may be taken as $W_X$, and may be used for the calculation of the ultraviolet light intensity ratio.

Similarly, the wavelength of the maximum absorption of chlorine trifluoride is 207 nm; thus, for example, the maximum value of ultraviolet light intensity of the wavelength region of less than 215 nm may be taken as $W_X$, and may be used for the calculation of the ultraviolet light intensity ratio. Further, the wavelength of the maximum absorption of iodine heptafluoride is 241 nm; thus, for example, the maximum value of ultraviolet light intensity of the wavelength region of less than 250 nm may be taken as $W_X$, and may be used for the calculation of the ultraviolet light intensity ratio.

Ultraviolet light emitted from the exit window of the gas cell 22 is measured with a spectroscope. The ultraviolet light emitted from the exit window may be introduced into the spectroscope via an optical fiber. When using a spectroscope, the absorption spectrum of the reference gas is measured by, for example, performing operation in conformity with a manual that comes with the product. When, for example, high-purity nitrogen gas is used as the reference gas and the reference gas is irradiated with ultraviolet light while using a filter so as to achieve the range of the ultraviolet light intensity ratio mentioned above, the absorption spectrum can be used as a blank because there is no absorption of nitrogen or the halogen fluoride in the wavelength region of less than 250 nm.

(2) Measurement of the Absorbance at a Wavelength of 285 nm of the Halogen Fluoride-Containing Gas The valve 16 is closed, the valve 14 is opened to introduce the halogen fluoride-containing gas into the gas cell 22 from the halogen fluoride-containing gas supply source 10, and the absorption spectrum of the halogen fluoride-containing gas is measured similarly to that of the reference gas mentioned above. At this time, a halogen fluoride-containing gas diluted with a diluent gas such as helium, argon, nitrogen, carbon dioxide, or carbon tetrafluoride may be introduced into the gas cell 22. The absorbance at a wavelength of 285 nm, which is the wavelength of the maximum absorption of fluorine, is measured from the absorption spectrum, and the concentration of fluorine gas is obtained by absorption spectrophotometry.

In terms of being able to make high-accuracy measurement, it is preferable that the absorption spectrum of the reference gas mentioned above be subtracted from the absorption spectrum of the halogen fluoride-containing gas, the absorbance at a wavelength of 285 nm be measured from the obtained absorption spectrum, and the concentration of fluorine gas be obtained by absorption spectrophotometry.

(3) Measurement Conditions

The temperature in the gas cell 22 when performing the measurement mentioned above is not particularly limited as long as it is not less than the temperatures at which the halogen fluoride-containing gas and the reference gas liquefy and solidify, but is preferably 20 to 150° C., and more preferably 50 to 120° C. If the temperature is higher than this range, the reaction between the halogen fluoride and each of the gas cell, and the entrance window and the exit window may progress, or the decomposition of the halogen fluoride may progress; thus, this is not preferable.

The pressure in the gas cell 22 when enclosing the halogen fluoride-containing gas and the reference gas mentioned above in the gas cell 22 and performing measurement is not particularly limited, but is preferably 0.01 to 0.2 MPaA, and more preferably 0.05 to 0.15 MPaA. If the pressure is lower than this range, the gas concentration mentioned above may be lowered, and sensitivity may be reduced; if the pressure is higher than this range, the apparatus may be damaged.

EXAMPLES

Hereinbelow, the present invention is described still more specifically on the basis of Examples; however, the present invention is not limited to these Examples.

Example 1

A bromine pentafluoride gas was used as the halogen fluoride-containing gas; using the analysis apparatus shown in the FIGURE, the concentration of fluorine gas contained in the bromine pentafluoride gas was measured in conformity with the measurement method of the present invention. As the gas cell 22, a gas cell in which the main body is made of SUS 316 and the entrance window and the exit window are formed of calcium fluoride was used.

First, nitrogen gas was used as the reference gas; nitrogen gas was introduced into the gas cell 22 from a high-purity nitrogen gas cylinder, which is the reference gas supply source 12; the maximum value of ultraviolet light intensity of the wavelength region of less than 225 nm was taken as $W_X$, and ultraviolet light of $W_X/W_F=1/20$ was irradiated onto the nitrogen gas in the gas cell 22 from a deuterium lamp (product name: L10290, manufactured by Hamamatsu Photonics K.K.) as the light source 18 via a short wavelength cut filter (product name: LU0250, manufactured by Asahi Spectra Co., Ltd.) as the filter 20. The absorption spectrum of ultraviolet light emitted from the gas cell 22 was measured with a multichannel spectroscope (product name: FLAME-S, manufactured by Ocean Optics, Inc.) as the spectroscope 24. The temperature in the gas cell was 50° C., and the pressure was 0.1 MPaA.

Next, the nitrogen gas in the gas cell 22 was discharged from the outlet 26; then, bromine pentafluoride gas was introduced into the gas cell 22 from the halogen fluoride-containing gas supply source 10; and under the conditions of the same temperature and the same pressure as those at the time of the reference gas measurement, ultraviolet light of $W_X/W_F=1/20$ was irradiated onto the bromine pentafluoride gas in the gas cell 22 from the light source via the filter mentioned above. Here, the absorption spectrum of ultraviolet light emitted from the gas cell 22 was measured with the spectroscope mentioned above. The absorption spectrum of the nitrogen gas was subtracted from the obtained absorption spectrum of the bromine pentafluoride gas, and the concentration of fluorine gas contained in the bromine pentafluoride gas was found. As a result, it was found that the concentration of fluorine was 2 volume ppm.

Example 2

The concentration of fluorine gas in iodine heptafluoride gas was found similarly to Example 1 except that iodine heptafluoride gas was used in place of the bromine pentafluoride gas as the halogen fluoride-containing gas, the maximum value of ultraviolet light intensity of the wavelength region of less than 250 nm was taken as $W_X$, and ultraviolet light of $W_X/W_F=1/18$ was irradiated. As a result, it was found that the concentration of fluorine was 3 volume ppm.

Example 3

The concentration of fluorine gas in chlorine trifluoride gas was found similarly to Example 1 except that chlorine trifluoride gas was used in place of the bromine pentafluoride gas as the halogen fluoride-containing gas and the maximum value of ultraviolet light intensity of the wavelength region of less than 215 nm was taken as $W_X$. As a result, it was found that the concentration of fluorine was 5 volume ppm.

Comparative Example 1

The concentration of fluorine gas contained in bromine pentafluoride gas was found similarly to Example 1 except that the filter was not used and ultraviolet light of $W_X/W_F=1/5$ was irradiated. As a result, it was found that the concentration of fluorine was 20 volume ppm and the decomposition reaction of bromine pentafluoride had progressed.

Comparative Example 2

The concentration of fluorine gas contained in iodine heptafluoride gas was found similarly to Example 2 except that the filter was not used and ultraviolet light of $W_X/W_F=1/5$ was irradiated. As a result, it was found that the concentration of fluorine was 24 volume ppm and the decomposition reaction of iodine heptafluoride had progressed.

Comparative Example 3

The concentration of fluorine gas contained in chlorine trifluoride gas was found similarly to Example 3 except that the filter was not used and ultraviolet light of $W_X/W_F=1/5$ was irradiated. As a result, it was found that the concentration of fluorine was 18 volume ppm and the decomposition reaction of chlorine trifluoride had progressed.

The conditions and results of Examples 1 to 3 and Comparative Examples 1 to 3 described above are shown in Table 1.

TABLE 1

|  | Halogen fluoride - containing gas | Ratio of ultraviolet light intensity ($W_X/W_F$) | Fluorine concentration (vppm) |
|---|---|---|---|
| Example 1 | bromine pentafluoride | 1/20 | 2 |
| Example 2 | iodine heptafluoride | 1/18 | 3 |
| Example 3 | chlorine trifluoride | 1/20 | 5 |
| Comparative example 1 | bromine pentafluoride | 1/5 | 20 |
| Comparative example 2 | iodine heptafluoride | 1/5 | 24 |
| Comparative example 3 | chlorine trifluoride | 1/5 | 18 |

REFERENCE SIGNS LIST 10 halogen fluoride-containing gas supply source
12 reference gas supply source
14 valve
16 valve
18 light source
20 filter
22 gas cell
24 spectroscope
26 outlet

The invention claimed is:

1. A method for measuring a concentration of fluorine gas, the method comprising:
   irradiating a halogen fluoride-containing gas with ultraviolet light in which a ratio ($W_X/W_F$) of a maximum value ($W_X$) of ultraviolet light intensity in a wavelength region of less than 250 nm with respect to an ultraviolet light intensity ($W_F$) at a wavelength of 285 nm is 1/10 or less; and
   measuring an absorbance at a wavelength of 285 nm to obtain a concentration of fluorine gas contained in the halogen fluoride-containing gas.

2. The method for measuring a concentration of fluorine gas according to claim 1, wherein
   using a means for suppressing irradiation with ultraviolet light of wavelengths of less than 250 nm, the halogen fluoride-containing gas is irradiated with ultraviolet light of wavelengths of not less than 250 nm from a light source.

3. The method for measuring a concentration of fluorine gas according to claim 1, wherein
   the means is to irradiate the ultraviolet light irradiated from the light source to the halogen fluoride-containing gas via a filter that blocks at least 50% of the ultraviolet light with a wavelength of less than 250 nm and transmits at least 90% of the ultraviolet light with a wavelength of 280-290 nm.

4. The method for measuring a concentration of fluorine gas according to claim 1, wherein
   the halogen fluoride is one kind of gas selected from the group consisting of chlorine trifluoride, bromine pentafluoride, iodine heptafluoride, bromine trifluoride, and iodine pentafluoride.

5. The method for measuring a concentration of fluorine gas according to claim 1, wherein
   the halogen fluoride is iodine heptafluoride.

6. The method for measuring a concentration of fluorine gas according to claim 1, wherein
   the halogen fluoride is bromine pentafluoride, and
   the maximum value ($W_X$) of ultraviolet light intensity in the wavelength region of less than 250 nm is a maximum value of ultraviolet light intensity in a wavelength region of less than 225 nm.

7. The method for measuring a concentration of fluorine gas according to claim 1, wherein
   the halogen fluoride is chlorine trifluoride, and
   the maximum value ($W_X$) of ultraviolet light intensity in the wavelength region of less than 250 nm is a maximum value of ultraviolet light intensity in a wavelength region of less than 215 nm.

8. The method for measuring a concentration of fluorine gas according to claim 1, wherein
   an absorption spectrum measured by irradiating a reference gas with the ultraviolet light is subtracted from an absorption spectrum measured by irradiating the halogen fluoride-containing gas with the ultraviolet light, and
   the concentration of fluorine gas is obtained from an absorbance at a wavelength of 285 nm of an obtained absorption spectrum.

* * * * *